(12) United States Patent
Wright et al.

(10) Patent No.: US 8,012,141 B2
(45) Date of Patent: Sep. 6, 2011

(54) SUCTION WAND

(76) Inventors: Clifford A. Wright, San Diego, CA (US); Robert F. Eisele, Carlsbad, CA (US)

( * ) Notice: Subject to any disclaimer, the term of this patent is extended or adjusted under 35 U.S.C. 154(b) by 220 days.

(21) Appl. No.: 12/333,829

(22) Filed: Dec. 12, 2008

(65) Prior Publication Data

US 2009/0204065 A1  Aug. 13, 2009

Related U.S. Application Data

(63) Continuation of application No. PCT/US2007/070789, filed on Jun. 8, 2007.

(60) Provisional application No. 60/908,745, filed on Mar. 29, 2007.

(51) Int. Cl.
*A61M 25/00* (2006.01)

(52) U.S. Cl. .............................................. 604/523

(58) Field of Classification Search ............. 604/6.16, 604/19, 35, 43–45, 48, 129, 242, 243, 263, 604/264, 513, 533, 540–542, 266
See application file for complete search history.

(56) References Cited

U.S. PATENT DOCUMENTS

| | | | |
|---|---|---|---|
| 2,522,381 A | 9/1950 | Kramer | |
| 2,994,457 A | 8/1961 | Fornas | |
| 3,388,705 A | 6/1968 | Grosshandler | |
| 4,050,466 A | 9/1977 | Koerbacher | |
| 4,061,226 A | 12/1977 | Essen | |
| 4,227,529 A | 10/1980 | Lomhold | |
| 4,287,889 A | 9/1981 | Stupar | |
| 4,291,691 A | 9/1981 | Cabal et al. | |
| 4,300,550 A | 11/1981 | Gandi et al. | |
| 4,439,884 A | 4/1984 | Giorni | |
| 4,468,216 A | 8/1984 | Muto | |
| 4,569,344 A | 2/1986 | Palmer | |
| 4,638,539 A | 1/1987 | Palmer | |
| 4,648,871 A | 3/1987 | Jacob | |
| 4,662,871 A | 5/1987 | Rafelson | |
| 4,676,749 A * | 6/1987 | Mabille | 433/88 |
| 4,696,296 A | 9/1987 | Palmer | |
| 4,748,007 A | 5/1988 | Gaudion et al. | |
| 4,795,447 A | 1/1989 | Dodson | |
| 4,813,538 A | 3/1989 | Blackman | |
| 4,825,859 A | 5/1989 | Lambert | |
| 4,834,726 A | 5/1989 | Lambert | |
| 4,836,199 A | 6/1989 | Palmer | |
| 4,850,350 A | 7/1989 | Jackson | |
| 4,872,579 A | 10/1989 | Palmer | |
| 4,921,488 A | 5/1990 | Maitz et al. | |
| 4,925,450 A * | 5/1990 | Imonti et al. | 604/240 |

(Continued)

OTHER PUBLICATIONS

United States Patent and Trademark Office, International Search Report and Written Opinion for PCT/US07/70789 dated Aug. 1, 2008.

*Primary Examiner* — Manuel A Mendez

(74) *Attorney, Agent, or Firm* — Perkins Coie LLP

(57) ABSTRACT

A suction wand assembly includes a suction wand connected to a valve assembly. The valve assembly includes a pressable button or similar device for allowing a user to regulate suction force through the suction wand. The valve assembly optionally includes a locking mechanism for holding the valve in a closed position. The suction wand assembly may be stored in a holster, which optionally includes an instrument support for holding a tip of the suction wand above a base region of the holster.

2 Claims, 6 Drawing Sheets

U.S. PATENT DOCUMENTS

| | | | |
|---|---|---|---|
| 4,938,741 A | 7/1990 | Lambert | |
| 4,967,743 A | 11/1990 | Lambert | |
| 5,002,534 A | 3/1991 | Rosenblatt | |
| 5,038,766 A | 8/1991 | Parker | |
| 5,062,835 A | 11/1991 | Maitz et al. | |
| 5,073,164 A | 12/1991 | Hollister et al. | |
| 5,083,561 A | 1/1992 | Russo | |
| 5,088,486 A | 2/1992 | Jinotti | |
| 5,101,817 A | 4/1992 | Etter | |
| 5,125,893 A | 6/1992 | Dryder | |
| 5,146,925 A * | 9/1992 | Snow | 600/435 |
| 5,167,622 A | 12/1992 | Muto | |
| 5,183,467 A | 2/1993 | Mouney | |
| 5,188,592 A | 2/1993 | Hakki | |
| 5,220,916 A | 6/1993 | Russo | |
| 5,254,098 A | 10/1993 | Ulrich et al. | |
| 5,255,676 A | 10/1993 | Russo | |
| 5,269,768 A | 12/1993 | Cheung | |
| 5,300,043 A | 4/1994 | Devlin et al. | |
| 5,309,902 A | 5/1994 | Kee et al. | |
| 5,325,850 A | 7/1994 | Ulrich et al. | |
| 5,333,607 A | 8/1994 | Kee et al. | |
| 5,337,780 A | 8/1994 | Kee | |
| 5,349,950 A | 9/1994 | Ulrich et al. | |
| 5,375,711 A | 12/1994 | Bree et al. | |
| 5,379,549 A | 1/1995 | Carcich et al. | |
| 5,431,637 A | 7/1995 | Okada et al. | |
| 5,454,131 A | 10/1995 | MacKenzie | |
| 5,460,613 A | 10/1995 | Ulrich et al. | |
| 5,471,706 A | 12/1995 | Wallock et al. | |
| 5,490,503 A | 2/1996 | Hollister | |
| 5,496,287 A | 3/1996 | Jinotti | |
| 5,578,006 A | 11/1996 | Schon | |
| 5,634,569 A | 6/1997 | DeCoster | |
| 5,643,230 A | 7/1997 | Linder | |
| 5,653,231 A | 8/1997 | Bell | |
| 5,676,136 A | 10/1997 | Russo | |
| 5,694,927 A | 12/1997 | Bohmfalk | |
| 5,713,849 A | 2/1998 | Bosma et al. | |
| 5,730,123 A | 3/1998 | Lorenzen et al. | |
| 5,730,727 A | 3/1998 | Russo | |
| 5,738,091 A | 4/1998 | Kee et al. | |
| 5,752,286 A | 5/1998 | Wright | |
| 5,779,687 A | 7/1998 | Bell et al. | |
| 5,788,680 A | 8/1998 | Linder | |
| D405,531 S | 2/1999 | Bonds | |
| 5,915,583 A | 6/1999 | Cloonan et al. | |
| 5,919,174 A | 7/1999 | Hanson | |
| 5,931,831 A | 8/1999 | Linder | |
| 6,012,451 A | 1/2000 | Palmer | |
| 6,070,582 A | 6/2000 | Kee | |
| 6,183,133 B1 | 2/2001 | Roegner | |
| 6,227,200 B1 | 5/2001 | Crump et al. | |
| 6,237,596 B1 | 5/2001 | Bohmfalk | |
| 6,299,116 B1 | 10/2001 | Levesque | |
| 6,334,865 B1 * | 1/2002 | Redmond et al. | 606/213 |
| 6,428,498 B2 | 8/2002 | Uflacker | |
| 6,436,085 B1 | 8/2002 | Lauer | |
| 6,494,203 B1 | 12/2002 | Palmer | |
| 6,551,278 B1 | 4/2003 | Geitz | |
| 6,588,425 B2 | 7/2003 | Rouns et al. | |
| 6,588,427 B1 | 7/2003 | Carlsen et al. | |
| 6,609,520 B1 | 8/2003 | Carlsen et al. | |
| 6,699,262 B2 * | 3/2004 | Redmond et al. | 606/213 |
| 6,769,430 B1 | 8/2004 | Carlsen et al. | |
| 6,923,184 B1 | 8/2005 | Russo | |
| 6,935,339 B2 | 8/2005 | Mattar Neto et al. | |
| 7,066,903 B2 * | 6/2006 | Yarger | 604/35 |
| 7,263,997 B2 | 9/2007 | Madsen et al. | |
| 7,527,058 B2 | 5/2009 | Wright et al. | |
| 2002/0172257 A1 | 11/2002 | Walls et al. | |
| 2007/0199846 A1 | 8/2007 | Wright | |
| 2007/0293812 A1 | 12/2007 | Wright | |

\* cited by examiner

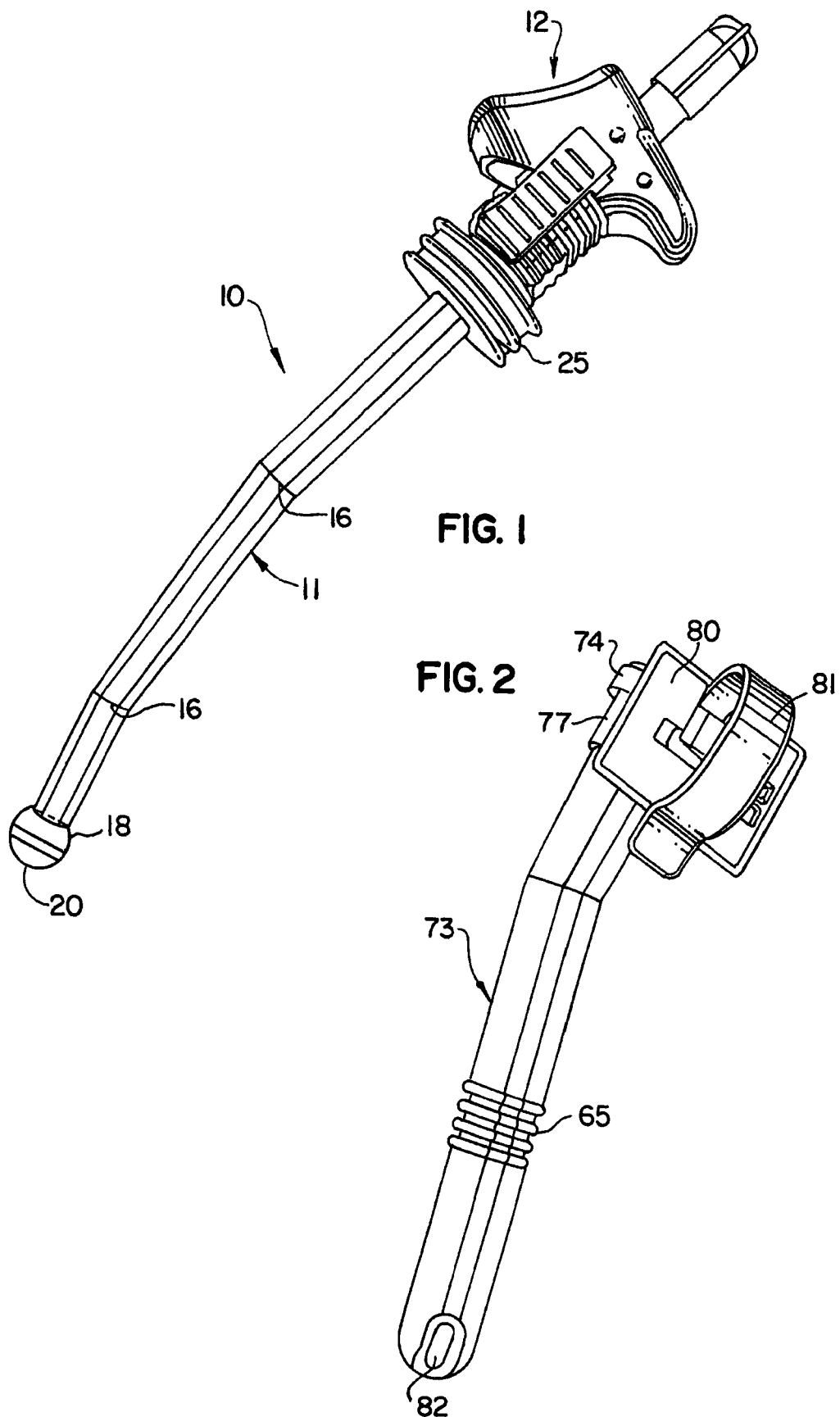

SUCTION WAND

CROSS-REFERENCE TO RELATED APPLICATIONS

This application is a continuation of International Application PCT/US2007/070789, filed Jun. 8, 2007 and now pending, which claims the benefit of: 1) U.S. Provisional Patent Application No. 60/908,745 filed Mar. 29, 2007; 2) U.S. Utility patent application Ser. No. 11/679,445 filed Feb. 27, 2007; and 3) U.S. patent application Ser. No. 11/424,200 filed Jun. 14, 2006, all of which are incorporated herein by reference.

BACKGROUND

Suction wands, such as Yankauer suction wands, are commonly used in oral cleansing and suctioning applications. Suction wands may be used for aspirating fluid and debris from a patient's mouth or from a surgical site, or for other medical or dental purposes. A typical suction wand includes one or more openings in a distal end or tip thereof through which fluids and other debris may be suctioned into the wand.

A typical suction wand is attached, via a hose or tube, to a suction canister, vacuum system, or other device providing a suctioning force. In many configurations, the suction tube includes an external opening near a region where the suction tubes connects to the suction wand. Ambient air is drawn through this external opening via the suctioning force of the suction device. When a medical attendant places a finger or thumb over this external opening, the suctioning force is directed to the one or more openings in the tip of the suction wand, allowing fluid or debris to be suctioned from a patient. When the medical attendant moves the finger or thumb away from the external opening in the tube, the primary suctioning force is re-directed to the external opening and little or no suctioning force is directed to the tip of the suction wand. In this manner, the medical attendant may control the suctioning force provided at the tip of the suction wand.

While existing suction wand systems have been relatively effective, a need exists for a suction wand with improved suction control capabilities.

SUMMARY

A suction wand assembly includes a suction wand connected to a valve assembly. The valve assembly includes a pressable button or similar device for allowing a user to regulate the suction force through the suction wand. The valve assembly optionally includes a locking mechanism for holding the valve in a closed position. The suction wand is optionally stored in a holster including an instrument support for supporting the wand in a position above the base of the holster.

Other features and advantages will appear hereinafter. The features described above can be used separately or together, or in various combinations of one or more of them.

BRIEF DESCRIPTION OF THE DRAWINGS

In the drawings, wherein the same reference number indicates the same element throughout the views:

FIG. 1 is a perspective view of a suction wand assembly, according to one embodiment.

FIG. 2 is a perspective view of a holster including internal instrument supports, according to one embodiment.

DETAILED DESCRIPTION OF THE DRAWINGS

Figure 3:
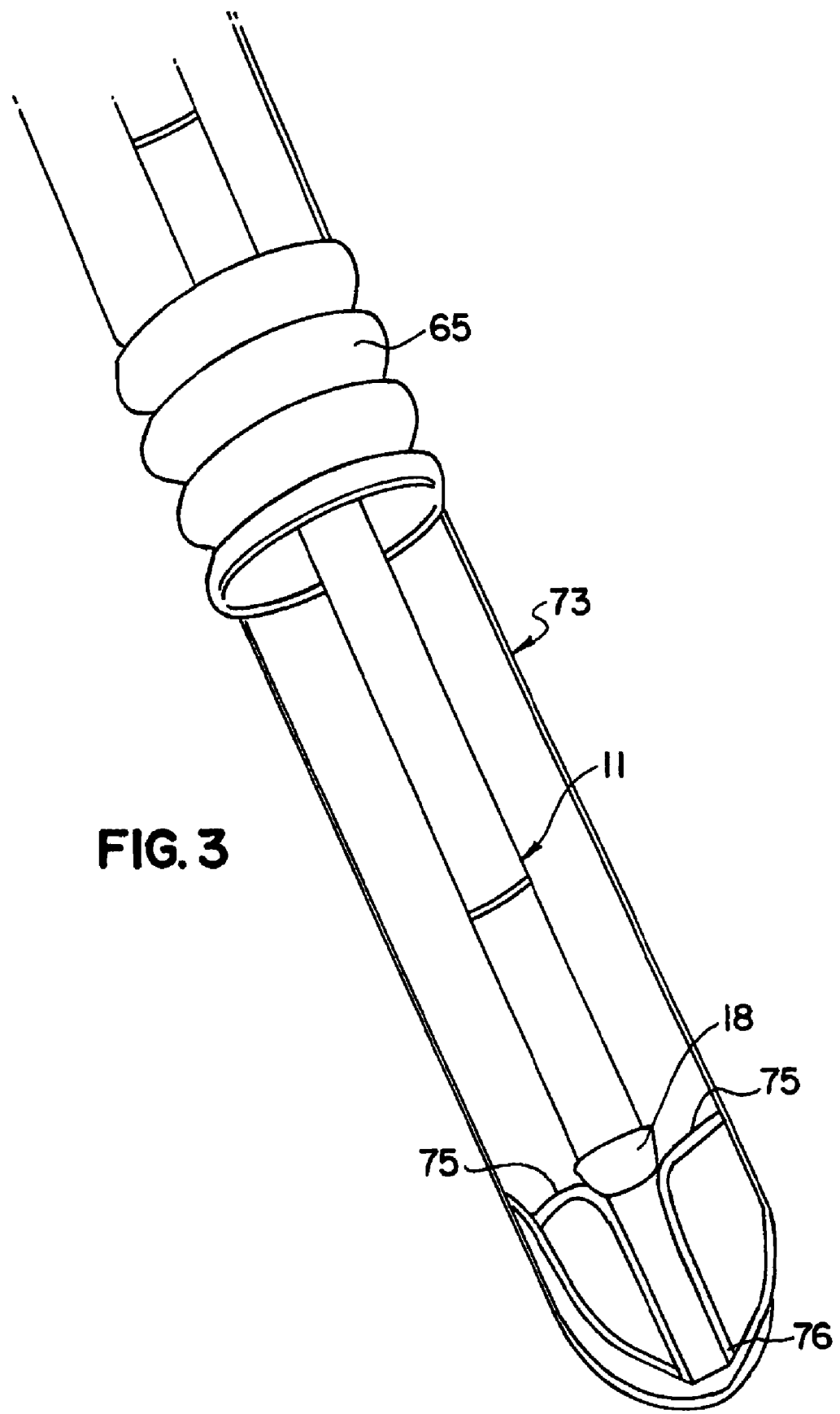
FIG. 3 is a partial perspective transparent view of the holster of FIG. 3 showing the instrument supports supporting an instrument.

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

Turning now in detail to the drawings, as shown in FIG. 1, a suction wand assembly 10 includes a suction wand 11 connected to a valve assembly 12. The body of the suction wand may be that of a conventional Yankauer suction wand or it may have any other suitable design. For example, as shown in FIG. 1, the suction wand 11 may include one or more bend points 16 to facilitate accessing various regions of a patient's mouth with the suction wand 11. The suction wand 11 may be made of a plastic, rubber, or any other suitable material. A distal end or tip 18 of the suction wand includes one or more openings 20 through which fluid or debris may be suctioned.

Figure 4:
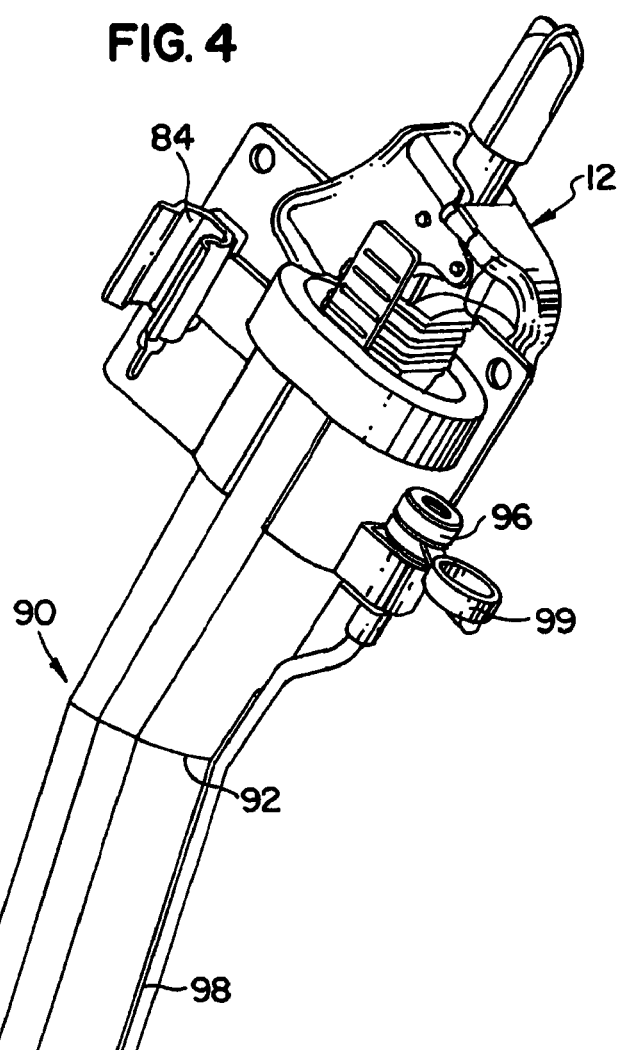
FIG. 4 is a perspective view of the suction wand assembly of FIG. 1 housed in an alternative embodiment of a holster.

Still referring to FIG. 1, the suction wand 11 optionally includes one or more raised rings or protrusions 25 on an outer surface thereof. The protrusions 25 are preferably located at or near a proximal end of the suction wand 11 adjacent to the valve assembly 12 but may be located at any other suitable location on the suction wand 11. The protrusions 25 are configured to fit snugly within, or to engage an inner surface of, a corresponding storage device, such as a suction wand holster, as shown in FIGS. 2-4. The protrusions 25 may be circular, oblong, elliptical, or any other shape configured to match the interior shape of the corresponding suction wand holster 73 or other suitable storage device.

In the embodiment illustrated in FIGS. 2 and 3, the suction wand holster 73 includes pleats 65, a bend, and one or more upwardly projecting ledges 75 or other instrument supports in a lower region thereof. The ledges 75 support the tip 18 of the suction wand 11 in a position above the base 76 of the holster 73 so that fluid and debris may fall from the wand tip 18 to the holster base 76. This is advantageous in that the suction wand 11 rests above, not within, any unsanitary fluid collected in the holster 73. Thus, the inclusion of one or more instrument supports in the holster 73 promotes sanitary conditions.

The one or more ledges 75 may be formed as part of the holster 73 itself, such as a "pinch" 82 of opposing walls of the closed end of the holster 73, or they may be one or more separate pieces adhered to or otherwise affixed to the interior of the holster 73. When the distal region includes a pinch 82, as shown in FIGS. 2 and 3, the pinch 82 forms two upwardly projecting ledges 75 upon which the tip 18 of the suction wand 11 may rest. While the inclusion of ledges 75 or other instrument supports is preferred, a holster not including instrument supports may be used to hold the suction wand assembly 10.

The holster 73 is preferably attachable to a clip 80 or other fastener (collectively referred to hereinafter as a "clip," for ease of reference) via a top lip 74 on a proximal end of the holster 73. The top lip 74 optionally slides over an outwardly protruding attachment piece 77 on the clip 80. The clip 80 is attachable to a bedrail, ventilator, hospital stand, wall, or other suitable object. As illustrated in FIG. 2, the clip 80 optionally includes an arm 81 defining an opening that allows the arm 81 to slide over a bedrail. The clip 80 may additionally or alternatively include one or more tie-straps for tying the clip 80 to an object, or may include an adhesive surface or pad for adhering the clip 80 to a wall or other object, or may include any other suitable attachment mechanism. As shown in FIG. 4, the clip 80 optionally includes a tube-holder 84 for securing a suction tube attached to the valve assembly 12.

FIG. 4 illustrates the suction wand assembly 1 0 housed in an alternative embodiment of a holster 90. The holster 90 includes a bend 92 and a plurality of inwardly projecting dimples 94 that provide instrument supports for the suction wand 11, similar to the ledges 75 shown in FIGS. 2 and 3. The holster 90 optionally includes a lavage housing 96 through which a cleaning fluid may be injected. The lavage housing 96 is in fluid communication with a tube 98 extending along an outer surface of the holster 90 and opening into the interior of the holster at a location above or adjacent to the dimples 94. Cleaning fluid injected by an attendant, via a syringe or other suitable device, into the lavage housing travels through the tube 98 and into the interior of the holster 90 at a location where the tip 18 of the suction wand 11 is supported. In this manner, the tip 18 of the suction wand 11 may be cleaned. The lavage housing 96 optionally includes a cap 99 for closing off the lavage housing 96 from outside environment when the lavage housing 96 is not in use.

Figure 5:
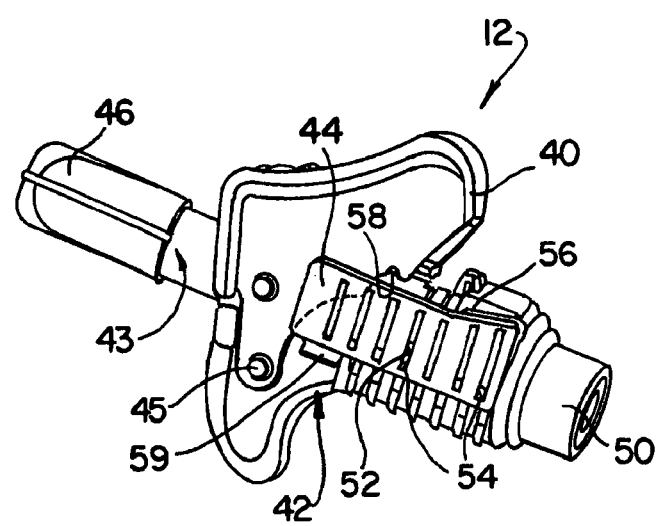
FIG. 5 is a side-perspective view of the valve assembly of the closed suction catheter shown in FIG. 1.
Figure 6:
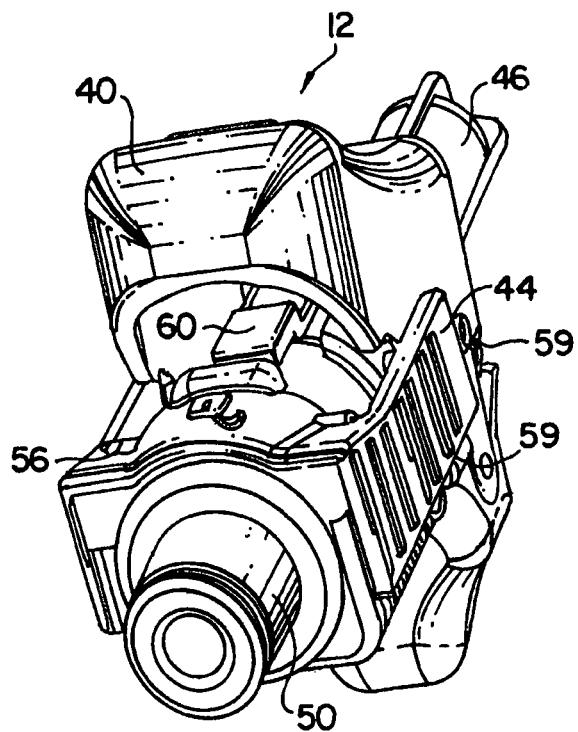
FIG. 6 is a front-perspective view of the valve assembly shown in FIG. 5.
Figure 7:
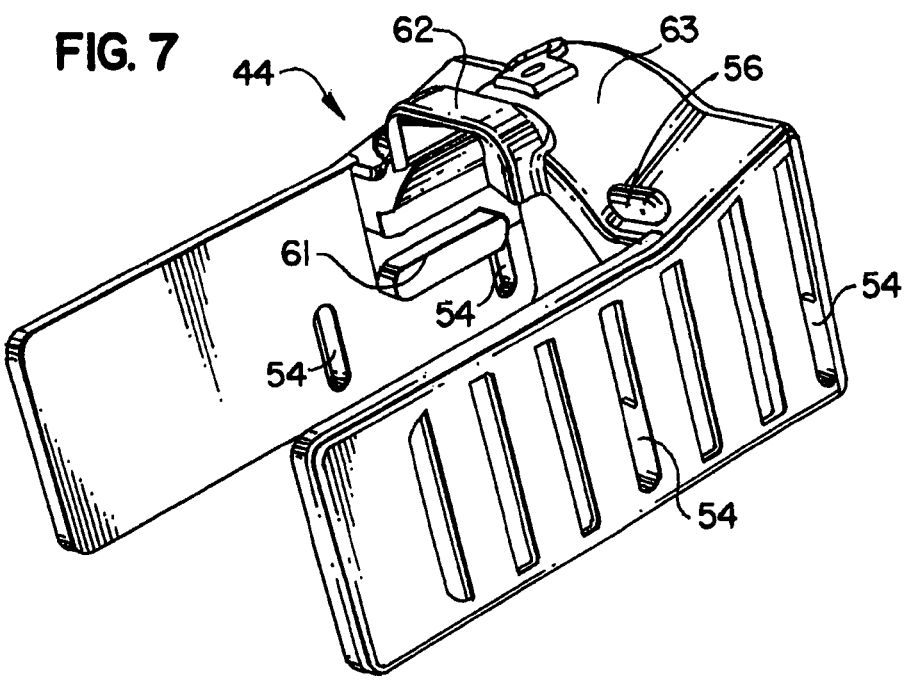
FIG. 7 is a perspective view of a locking mechanism of the valve assembly shown in FIGS. 5 and 6.
Figure 8:
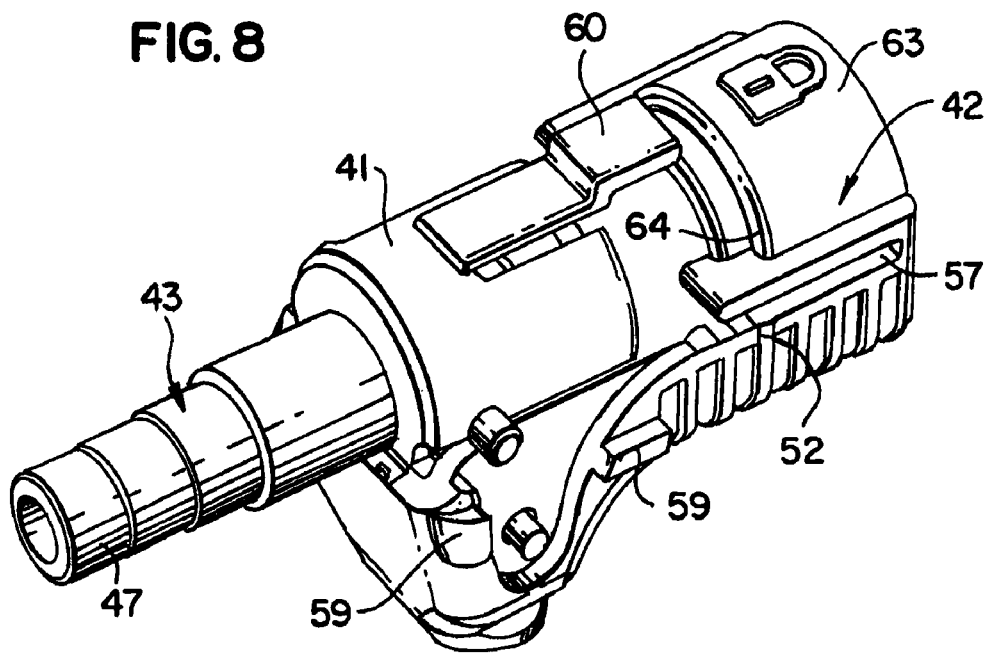
FIG. 8 is a perspective view of the valve stem, valve body, and cam arm components of the valve assembly shown in FIGS. 5-7.

Referring to FIGS. 5-10, the valve assembly 12 includes a button 40 or other actuator pivotally attached to a valve body 42 via a pin 45 or other suitable connector. The button 40 is biased into an "up" position (as shown in FIGS. 5 and 6) via a spring-loaded retainer 41 or other suitable biasing mechanism. A valve stem 43, which may be disposed within the spring of the retainer 41, is attached to an underside of the retainer 41. A barb cap 46 may be included on a barb portion 47 of the valve stem 43 for covering the barb portion 47 when it is not in use, i.e., when it is not connected to suction tubing associated with a vacuum system or other suction system.

By including the barb portion 47 directly on the valve stem 43, the barb portion 47 moves in unison with the valve stem 43 when the button 40 is pressed, and the number of components required to make up the valve assembly 12 is reduced. Furthermore, the efficiency of the suctioning process is increased, since components commonly used in valve systems where the hose barb is separate from the valve stem, such as a suction plunger valve, are not required. Thus, there is less "dead" vacuum or suction space, and a constant flow of suctioning air is provided between the valve stem 43 and the barb portion 47. A substantially cylindrical member 50 or other suitable structure protrudes from the valve body 42 for connection to the suction wand 11. The suction wand 11 may alternatively be connected to the valve assembly 12 in any other suitable manner.

Pressing down on the button 40 actuates the retainer 41 and moves the valve stem 43 toward the suction wand 11 (from left to right in FIG. 5), which opens the valve and provides a suctioning force through the suction wand 11 when the barb portion 47 of the valve stem 43 is connected to a vacuum system or other suction system (via suction tubing or a similar connector). In this manner, the suction wand 11 may be used to suction fluid or debris from a patient's mouth or other medical site.

The valve assembly 12 preferably includes a locking mechanism for maintaining the button 40 in the "up" or locked position when the valve assembly 12 is not in use. The locking mechanism optionally includes a slider unit 44 slidably or otherwise movably secured to the valve body 42. The slider unit 44 includes internal guide rails 61 for engaging corresponding external channels 57 on the valve body 42. This configuration promotes smooth sliding movement of the slider unit 44 while maintaining it in a level, properly aligned position.

The valve body preferably includes one or more outwardly projecting steps or ribs 52 for engagement with one or more corresponding openings 54 on the slider unit 44. In the embodiment shown, each side of the valve body 42 includes one rib 52 for separately engaging one of two openings 54 (which correspond to unlocked and locked positions) present on each side of the slider unit 44. In the illustrated position, a rib 52 on each side of the valve body engages an approximately central opening 54 (the leftmost opening in FIGS. 5 and 7) on the slider unit 44 to releasably hold the slider unit 44 in the open position. By forcing the slider unit 44 toward the barb cap 46 on the valve stem 43 (from right to left in FIG. 5), the walls of the slider unit 44 deflect slightly outwardly such that the approximately central opening 54 disengages from the rib 52 on each side of the valve body 42. The slider unit 44 continues to move in that direction until an opening 54 near the inner end (the right end in FIGS. 5 and 7) of the slider unit 44 passes over, and is engaged by, the rib 52 on each side of the valve body 42.

In this "locked" position, one or more ribs or steps 56 on an upper portion of the slider unit 44 may engage corresponding lower grooves 58 in the button 40 to help maintain the button in the "up" or locked position. Additionally, one or more outwardly projecting ledges 59 may be included on one or both sides of the valve body 42, below the slider unit 44, to inhibit downward movement of the slider unit 44 when the valve is in the locked position.

The spring-loaded retainer 41 includes a cam arm 60 extending over a portion of the valve stem 43 and the valve body 42. When the slider unit 44 is moved from the unlocked to the locked position (from right to left in FIG. 5), a central cover or hood 63 on the slider unit 44 forces the cam arm 60 downwardly such that the face of the free end of the cam arm 60 engages an inward-facing ridge 64 on the valve body 42. In this manner, the retainer 41 and valve stem 43 are prevented from moving into the open position (from left to right in FIG. 5), which significantly minimizes or eliminates leaks in the valve assembly 12. The central hood 63 preferably includes an elevated region 62 for initially accepting the cam arm 60 and guiding the cam arm 60 toward the interior portion of the central hood 63 that downwardly deflects the cam arm 60.

Thus, the locking mechanism may include one or more locking devices, including but not limited to the following: ribs 52 on the valve body 42 that engage corresponding openings 54 in the slider unit 44; steps 56 on the slider unit 44 that engage corresponding grooves 58 in the button 40; ledges 59 for maintaining the slider unit 44 in the proper vertical position; and a cam arm 60 on the retainer 41 for engagement with a ridge 64 on the valve body 42. As a result, the valve assembly 12 may be securely and safely held in the locked or closed position, while remaining readily movable between the locked and unlocked positions.

Figure 9:
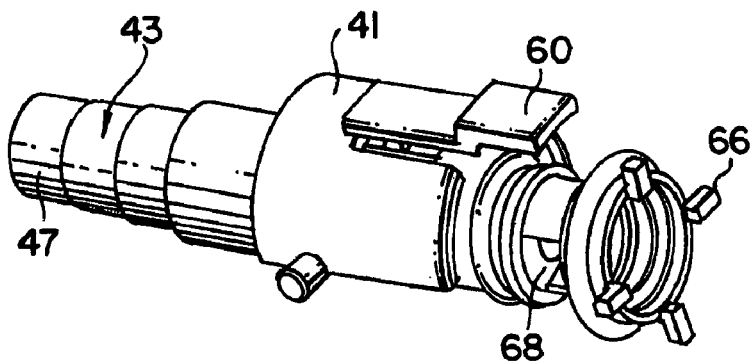
FIG. 9 is a perspective view of the valve stem and cam arm components shown in FIGS. 7 and 8.
Figure 10:
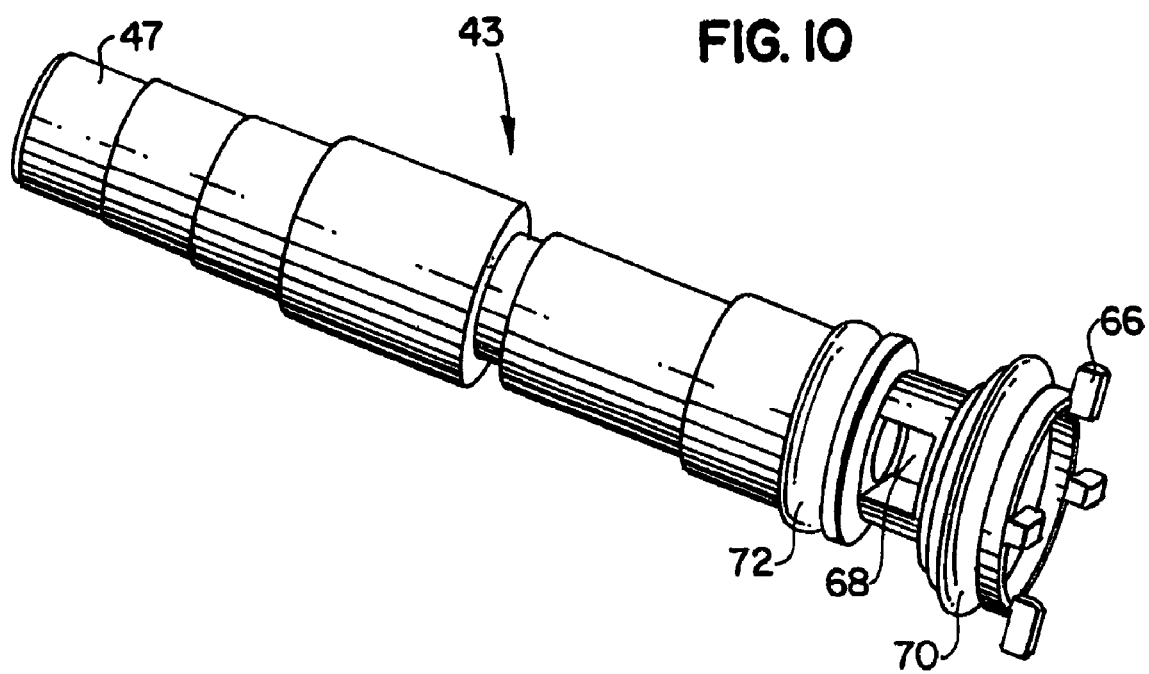
FIG. 10 is a side-perspective view of the valve stem shown in FIGS. 7-9.

Referring to FIGS. 9 and 10, the valve stem 43 preferably includes multiple outwardly projecting legs 66 for centering the valve stem 43 within the valve body 42. The legs 66 are configured to fit closely within the valve body 42 so that the valve stem 43 remains at least substantially straight and aligned (i.e., does not become angled relative to the longitudinal axis of the valve body 42) within the valve body 42. By maintaining the valve stem 43 in proper alignment within the valve body 42, the valve opens smoothly and efficiently when the button 40 is pressed. In many existing valve systems (for example, those used with closed suction catheter systems), the valve stem may readily become misaligned, which may lead to leaking and reduced suction capabilities.

The valve stem 43 includes one or more openings 68 through which air is suctioned when the valve stem 43 is moved into the unlocked or open position. By providing a relatively large opening through the valve stem 43, a large vacuum or suctioning force may be created while producing minimal audible noise. The valve stem 43 preferably includes a first O-ring 70 or other suitable seal on a first side of the opening 68, and a second O-ring 72 or other suitable seal on a second side of the opening 68, for sealing with the interior of the valve body 42.

In use, the barb portion 47 of the valve stem 43 is connected, via suction tubing or a similar connector, to a vacuum system or other suction system. If the slider unit 44 on the locking mechanism is in the locked position, the attendant slides the slider unit 44 into the unlocked position and presses and holds the button 40 to open the valve and create a suctioning force through the one or more openings 20 in the tip 18 of the suction wand 11. The attendant places the suction wand 11 into the patient's mouth or other medical site. The suctioning force causes fluid or debris to flow into the suction wand 11.

After the suctioning process is complete, the attendant withdraws the suction wand 13 from the patient's mouth or other medical site. The attendant may then slide the slider unit 44 into the locked position so that inadvertent pressing of the button 40 is prevented, and so that the valve stem 43 is held securely in place by the cam arm 60. The suction wand assembly 10 may be placed in the holster 73 when not in use.

The suction wand assembly 10 provides a readily controllable suctioning process via use of the valve assembly 12, which provides a consistent suctioning force. Furthermore, use of the locking mechanism on the valve assembly 12 ensures the valve assembly 12 remains closed when desired.

Any of the above-described embodiments may be used alone or in combination with one another. Furthermore, the suction wand assembly may include additional features not described herein. While several embodiments have been shown and described, various changes and substitutions may of course be made, without departing from the spirit and scope of the invention. The invention, therefore, should not be limited, except by the following claims and their equivalents.

What is claimed is:

1. A suction wand assembly, comprising:
   a suction wand including a distal end having a tip and a proximal end;
   a user-actuatable valve assembly connected to the proximal end of the suction wand, wherein the valve assembly comprises:
   a valve body;
   a valve stem within the valve body;
   a button for actuating the valve stem; and
   a locking mechanism for maintaining the button in a locked position,
   wherein the locking mechanism comprises:
   a cam arm;
   a slider unit movable along the valve body between a locked position, in which the slider unit deflects the cam arm into engagement with the valve body to prevent movement of the valve stem, and an unlocked position.

2. The suction wand assembly of claim 1 wherein the locking mechanism further comprises at least one rib on the valve body configured to engage corresponding openings on the slider unit for maintaining the slider unit in the locked and unlocked positions.

* * * * *